March 15, 1955 G. JAMES Plant Pat. 1,361
PECAN TREE
Filed Jan. 13, 1950
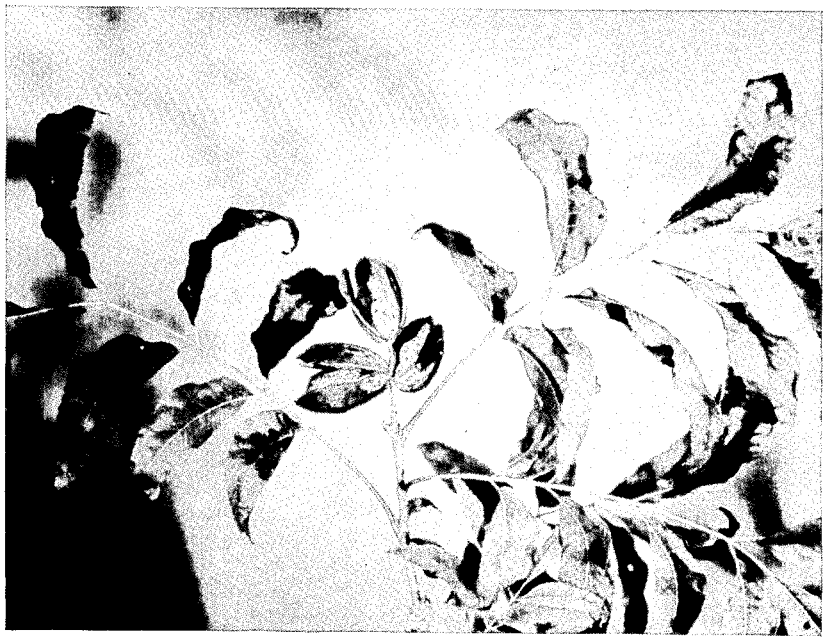
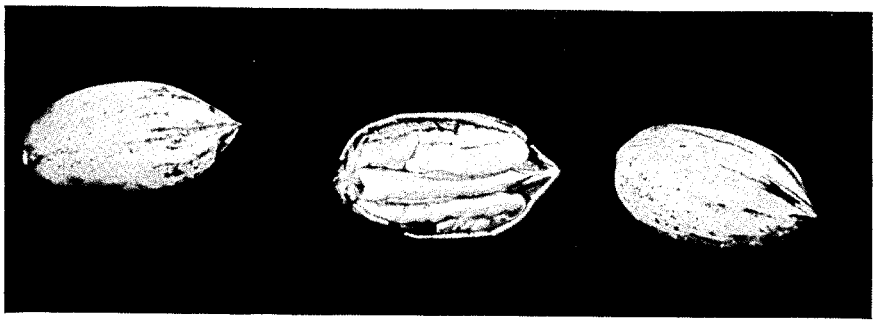
Inventor.
George James
By Robbs & Robbs
Attorneys.

United States Patent Office

Plant Pat. 1,361
Patented Mar. 15, 1955

1,361

PECAN TREE

George James, Brunswick, Mo., assignor to Stark Bro's Nurseries and Orchards Company, Louisiana, Mo., a corporation of Missouri Application January 13, 1950, Serial No. 138,407

1 Claim. (Cl. 47—62)

The present discovery relates to a new and distinct variety of pecan tree, originating on my property at Brunswick, Missouri, as a selected, cultivated seedling which sprouted amongst an experimental plot of native pecan trees of unidentified parentage, after said plot had been cleared completely of all underbrush, thinned out to preserve those trees having the best nuts and other most desirable characteristics, and thereafter cultivated to establish the grove in which the new variety was grown to maturity.

My attention was particularly directed and devoted to this particular new seedling because it bore true paper shell nuts comparable to those Southern type pecans which normally do not extend beyond the territory 300 to 500 miles farther south than the location of my property. While preserving all the favorable features of Southern type pecans, but with an improved and superior flavor, my new variety makes it possible to extend the Northern limits of Southern type pecans far beyond the former limits, all resulting from my cultivation and care of my experimental plot in which I discovered this new seedling, and but for which the new variety would have been lost to mankind.

This new variety is distinct from and superior to other pecans adapted to the Northern pecan areas in that the nuts borne thereby are much larger than "Indiana" (unpatented), have a thinner shell, and the kernels are plump and solid, separate cleanly from the shell and are of exceptionally good quality, with a more distinct pecan flavor than "Stuart" (unpatented) and other Southern pecans. The new variety is extremely hardy, having withstood temperatures as low as 20° below zero without injury, requires a comparatively short growing season, and the nuts mature during the last week of September at Brunswick, Missouri, which is about two weeks before the average date of killing frosts in this region.

These distinctive tree and nut characteristics represent a marked improvement in pecan trees, and said characteristics have been found to be established and fixed by asexual reproduction of the variety by both grafting and budding at Brunswick, Missouri.

The drawing illustrates specimens of the new pecan tree foliage and nuts, the latter being shown in both elevation and in section.

The following is a detailed description of the new variety, giving color designations according to Ridgway's Color Standards and Nomenclature (observations were made near Brunswick, Missouri).

Dates first and lasting picking: September 24th–September 30th.

Seedling: Seed and pollen parents—unknown.

Propagation: Holds its distinguishing characteristics through succeeding propagations.

Maturity season: September 24th.

Tree: Medium size; vigorous; hardy.

*Productivity.*—Medium productive.

*Growth.*—Vigorous; upright; spreading. Limbs—slim.

*Wood.*—Color (1 year)—Wood Drab, Plate XLVI, Color No. 17'''' (Ridgway).

*Foliage.*—Abundant; large. Leaves coarsely serrate—leaflets 6" x 1½". Leaves 11" to 13" long.

*Buds.*—Long; pointed. Color—Blister, Plate XXIX, Color No. 15" tome *m* (Ridgway).

Nuts:

*Ripening.*—Even. Time of harvesting—September 20th–September 24th.

*Quantity.*—Medium abundant.

*Maturity.*—Early.

*Tenacity.*—Free.

*Cluster.*—Average number of nuts to cluster—3. Size—large.

*Size.*—Length—1⅝". Diameter—⅞" x 13/16".

*Weight.*—Average number of nuts to pound—64.

*Shape.*—Oblong; compressed toward point. Base—round. Point—Mucronate.

*Shell.*—Thin; cracks and releases easily. Color—Wood Brown, Plate XL, Color No. 17''' (Ridgway), with black markings mostly toward tip.

*Kernel.*—Flavor—good. Shape—halves are oblong with short point — thick. Texture—firm. Sutures—even.

I claim:

A new and distinct variety of pecan tree, characterized as to novelty by its extreme hardiness, requisite short growing season and early maturity of the nuts which are of large size and thin shell, separating cleanly from the kernels which are plump and solid and of superior quality, with a more distinct pecan flavor than Southern pecans, substantially as shown and described.

References Cited in the file of this patent

UNITED STATES PATENTS

| | | |
|---|---|---|
| Pl. Pt. 47 | Brake | Nov. 29, 1932 |
| Pl. Pt. 73 | Simpson | July 25, 1933 |
| Pl. Pt. 510 | Harris | Apr. 28, 1942 |
| Pl. Pt. 833 | Harris | Apr. 26, 1949 |

OTHER REFERENCES

The Wise Encyclopedia, Ed. by E. L. D. Seymour B. S. A., Wm. H. Wise Co., Inc., New York, 1951 (pages 949 to 951).